（12）United States Patent
Graneto et al.

(10) Patent No.: US 7,772,269 B2
(45) Date of Patent: Aug. 10, 2010

(54) PYRAZOLE ANALOGS

(75) Inventors: Mathew J. Graneto, Chesterfield, MO (US); Todd M. Maddux, Foristell, MO (US); Jaime L. Masferrer, Chesterfield, MO (US)

(73) Assignee: Pfizer Inc., New York, NY (US)

( * ) Notice: Subject to any disclaimer, the term of this patent is extended or adjusted under 35 U.S.C. 154(b) by 308 days.

(21) Appl. No.: 11/944,732

(22) Filed: Nov. 26, 2007

(65) Prior Publication Data

US 2008/0125474 A1 May 29, 2008

Related U.S. Application Data

(60) Provisional application No. 60/867,337, filed on Nov. 27, 2006.

(51) Int. Cl.
*A61K 31/4155* (2006.01)
*C07D 231/12* (2006.01)
*C07D 309/08* (2006.01)

(52) U.S. Cl. ............... 514/406; 548/365.7; 549/425

(58) Field of Classification Search ......... 548/365.7; 514/406; 549/425
See application file for complete search history.

(56) References Cited

U.S. PATENT DOCUMENTS 5,276,037 A * 1/1994 Dowell et al. ......... 514/252.01
5,883,106 A   3/1999 Stevens et al. ............ 514/277

FOREIGN PATENT DOCUMENTS

EP       0787127      1/2001
WO       WO 9429299   12/1994
WO       WO 9711079   3/1997

OTHER PUBLICATIONS

Peters-Golden et al. The New England Journal of Medicine 2007, 357(18), 1841-1854.*
Schafer et al. Drug Discovery Today 2008, 13 (21/22), 913-916.*
Horig et al. Journal of Translational Medicine 2004, 2(44).*
Drazen et al., New England Journal of Medicine, "Treatment of Asthma with Drugs Modifying the Leukotriene Pathway," vol. 340, pp. 197-206, 1999.

* cited by examiner

*Primary Examiner*—Rebecca L Anderson
*Assistant Examiner*—Jason M Nolan
(74) *Attorney, Agent, or Firm*—Gregg C. Benson; Robert T. Ronau

(57) ABSTRACT

The invention relates to the compounds of formula (I):

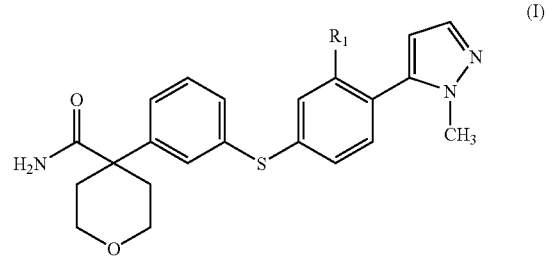

or a pharmaceutically acceptable salt and solvate thereof, wherein $R_1$ is F or H and to processes for the preparation of, intermediates used in the preparation of, compositions containing the uses of, such compounds. The compounds according to the present invention are useful in numerous diseases, disorders and conditions, in particular allergic and respiratory diseases, disorders and conditions.

13 Claims, No Drawings

PYRAZOLE ANALOGS

FIELD OF THE INVENTION

The present invention relates to compounds, compositions, and methods for treating diseases and conditions. In particular, the invention relates to compounds, compositions, and methods for treating allergic and respiratory diseases, disorders and conditions. The invention further relates to a compound of formula (I):

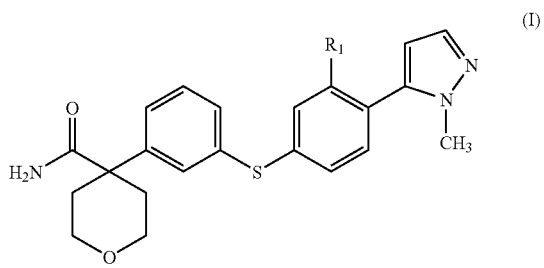

or a pharmaceutically acceptable salt and solvate thereof, wherein $R_1$ is F or H.

In particular, the present invention relates to 4-(3-{[3-fluoro-4-(1-methyl-1H-pyrazol-5-yl)phenyl]thio}-phenyl)tetrahydro-2H-pyran-4-carboxamide and to 4-(3-{[4-(1-methyl-1H-pyrazol-5-yl)phenyl]thio}phenyl)tetrahydro-2H-pyran-4-carboxamide and to pharmaceutically acceptable salts and solvates of each of these compounds and to processes for the preparation of, intermediates used in the preparation of, compositions containing and the uses of such compounds.

BACKGROUND OF THE INVENTION

The leukotrienes (LT) are a group of highly potent lipid mediators that play critical roles in numerous diseases, including inflammatory diseases and allergic disease states (Samuelsson, B., 1983, Leukotrienes: Science 220, 568-575). The enzyme 5-lipoxygenase (5-LO) converts arachidonic acid into the leukotriene $A_4$ ($LTA_4$) which may then be hydrolyzed into leukotriene $B_4$ ($LTB_4$) by the enzyme $LTA_4$ hydrolase, or may react to form leukotriene $C_4$ ($LTC_4$) by a catalytic reaction mediated by $LTC_4$ synthase.

Leukotrienes $B_4$, $C_4$, $D_4$, and $E_4$ have been shown experimentally to play a role in the inflammation involved in asthma. In addition, inhaled $LTC_4$ and leukotriene $D_4$ ($LTD_4$) have been reported to be the most potent bronchoconstrictors yet studied in human subjects. $LTC_4$ and $LTD_4$ have also been reported to possibly cause migration of inflammatory cells into asthmatic airways (O'Byrne, Chest, Vol 111, (2):27).

Activation of the 5-lipoxygenase (5-LO) pathway leads to the biosynthesis of a number of proinflammatory leukotriene lipid mediators. The critical role of leukotrienes in allergic and respiratory diseases has been demonstrated using several animal models of LT deficiency, particularly 5-LO knock-out mice (Leuchron Contract No. QLG1-CT-2001-01521, Review, The Leukotrienes: Signaling Molecules in Chronic and Degenerative Diseases: Byrum, R. S., Goulet, J. L., Snouwaert, J. N., Griffiths, R. J. & Koller, B. H. (1999), *J Immunol* 163, 6810-6819. Bailie, M. B., Standiford, T. J., Laichalk, L. L., Coffey, M. J., Strieter, R. & Peters-Golden, M. (1996), *J. Immunol.* 157, 5221-5224). In addition, drugs that interfere with the biosynthesis and action of LTs have been marketed as novel medications against asthma and allergic rhinitis (Drazen, J. F., Israel, E. & O'Byrne, P. (1999), *N. Engl. J. Med.* 340, 197-206). For a review article on lipoxygenase inhibitors, see H. Masamune and L. S. Melvin, Sr.: Annual Reports in Medicinal Chemistry, 1989, 24, pp 71-80 (Adademic).

In particular, 4-(3-(4-(2-methyl-1H-imidazol-1-yl)phenylthio)phenyl)-tetrahydro-2H-pyran-4-carboxamide was previously tested in human clinical trials (U.S. Pat. No. 5,883,106 and EP 0787127).

There is a need to provide new 5-LO inhibitors that are good drug candidates. Such 5-LO inhibitors should show good potency, possess high levels of selectivity, and have properties particularly suitable for providing effective treatment while minimizing or eliminating side-effects.

SUMMARY OF THE INVENTION

Compounds have now been found that are potent and selective inhibitors of 5-LO, and provide superior side effect profiles to those compounds known in the art.

In one embodiment of the present invention there is provided a compound of formula (I):

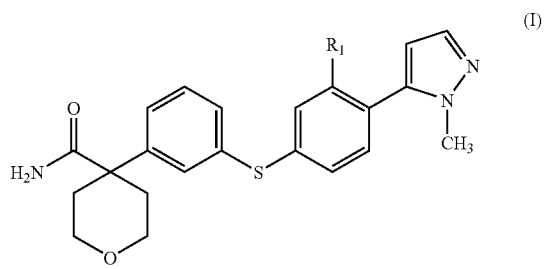

or a pharmaceutically acceptable salt and solvate thereof, wherein $R_1$ is F or H.

In another embodiment of the present invention, there is provided a compound of formula (Ia):

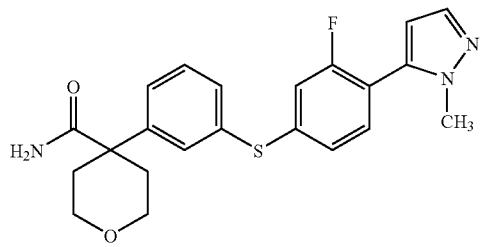

and pharmaceutically acceptable salts and solvates thereof.

Another embodiment of the present invention is directed to a compound of formula (Ib):

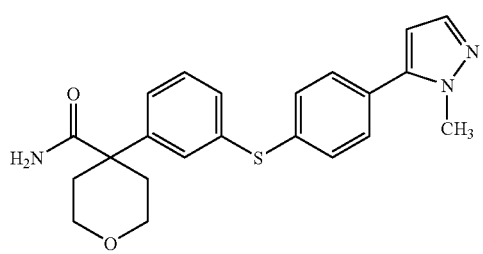

and pharmaceutically acceptable salts and solvates thereof.

In another embodiment of the present invention, there is provided a compound of formula (V), useful as synthetic intermediate for the manufacture of a compound of formula (Ia)

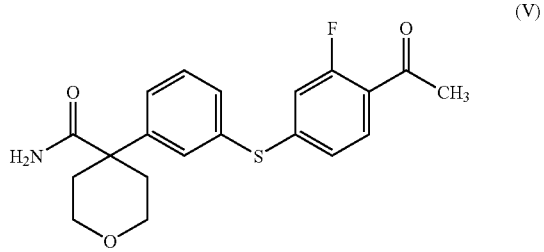

In another embodiment, the present invention relates to a compound of formula (Ia) or (Ib) or pharmaceutically acceptable salts and solvates thereof, as defined above, for use as a medicament.

Another embodiment of the present invention is directed to a method of treating a disease, disorder, or condition, wherein the disease, disorder or condition is selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolitis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupous bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

in a subject in need of such treatment, comprising administering to said subject a compound of formula (Ia) or (Ib) or pharmaceutically acceptable salts and solvates thereof.

Another embodiment of the present invention is directed to the use of a compound of formula (Ia) or (Ib) or pharmaceutically acceptable salts and solvates thereof in the manufacture of a medicament for the treatment of a disease, disorder or condition selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolitis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupous bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

Still another embodiment of the present invention is directed to the use of a compound of formula (Ia) or (Ib) or pharmaceutically acceptable salts and solvates thereof for use in treating a 5-LO mediated disease, disorder or condition.

One embodiment of the present invention is directed to the use of a compound of formula (Ia) or (Ib) or pharmaceutically acceptable salts and solvates thereof in the manufacture of a medicament for the treatment of a 5-LO-mediated disease, disorder or condition.

Another embodiment of the present invention is directed to a pharmaceutical composition comprising a compound of formula (Ia) or (Ib) or pharmaceutically acceptable salts and solvates thereof, and a pharmaceutically acceptable excipient.

Another embodiment of the present invention provides a process for the preparation of a compound of formula (Ia) wherein said process comprises contacting 2,4-difluoroacetophenone with 4-{3-[(triisopropylsilyl)thio]phenyl}-tetrahydro-2H-pyran-4-carboxamide in the presence of a suitable base and in the presence of a suitable solvent, optionally with a suitable additional reagent to remove the protecting group, for an appropriate time and temperature to produce 4-(3-{[3-fluoro-4-(1-methyl-1H-pyrazol-5-yl)phenyl]thio}phenyl)-tetrahydro-2H-[pyran-4-carboxamide; contacting 4-(3-{[3-fluoro-4-(1-methyl-1H-pyrazol-5-yl)phenyl]thio}phenyl) tetrahydro-2H-[pyran-4-carboxamide with at least one suitable reagent to facilitate pyrazole formation to produce the compound of formula (Ia).

Another embodiment of the present invention provides a process for the preparation of a compound of formula (Ib) wherein the process comprises:

contacting 4-(3-Bromophenyl)-tetrahydro-2H-pyran-4-carboxamide with at least one suitable reagent to facilitate pyrazole formation to produce a compound of formula 5-(4-bromophenyl)-1-methyl-1H-pyrazole; and then contacting the 5-(4-bromophenyl)-1-methyl-1H-pyrazole with a compound of 4-{3-[(tri-isopropylsilyl)thio]phenyl}tetrahydro-2H-pyran-4-carboxamide in the presence of a suitable catalyst to form a compound of formula (Ib).

Other and further embodiments will occur to those skilled in the art in light of this disclosure.

DETAILED DESCRIPTION OF THE INVENTION

Unless otherwise indicated, in the present invention the language "a compound of formula (Ia) or (Ib) or pharmaceutically acceptable salts and solvates thereof" or "a compound of formula (Ia) or (Ib) or a pharmaceutically acceptable salt and solvate thereof" is intended to identify a compound selected from the group consisting of: a compound of formula (Ia), a pharmaceutically acceptable salt of a compound of formula (Ia), a pharmaceutically acceptable solvate of a compound of formula (Ia), a pharmaceutically acceptable solvate of a pharmaceutically acceptable salt of a compound of formula (Ia), a compound of formula (Ib), a pharmaceutically acceptable salt of a compound of formula (Ib), a pharmaceutically acceptable solvate of a compound of formula (Ib) and a pharmaceutically acceptable solvate of a pharmaceutically acceptable salt of a compound of formula (Ib).

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition. Non-limiting examples include reduction in pain, discomfort, swelling or fever.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Non-limiting examples include administration of the compound or combination to a subject simultaneously with, prior to, or subsequent to surgery; and administration of the compound or combination with a further combination of drugs or agents. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, inhibition of progressive nerve destruction, reduction of biomarkers associated and correlated with diseases or disorders, and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

"Compounds of the invention" or "a compound of the invention" as used herein, unless otherwise specified, means a compound of formula (Ia) or (Ib) or a pharmaceutically acceptable salt and solvates thereof, as defined above, and an isotopically-labeled compound of formula (Ia) or of a compound of formula (Ib).

In the present invention, when there is doubt as to the agreement of the chemical name and the chemical structure, the chemical structure governs the description of the compound in question.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Compounds of the invention may also exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^{31} K^+$, or $—SC_3^-Na^+$) or non-ionic (such as $—N^-N^+(CH_3)_3$) polar head group. For more information, see *Crystals and the Polarizing Microscope* by N. H. Hartshorne and A. Stuart, 4$^{th}$ Edition (Edward Arnold, 1970).

Also included within the scope of the invention are metabolites of compounds of formula I, that is, compounds formed in vivo upon administration of the drug. Some examples of metabolites in accordance with the invention include:
 (i) an hydroxymethyl derivative of methyl groups ($—CH_3$—>$—CH_2OH$):
 (ii) a secondary amino derivative of tertiary amino groups, ($—NR^1R^2$—>$—NHR^1$ or $—NHR^2$)
 (iii) a phenol derivative of phenyl moieties (—Ph->—PhOH); and
 (iv) a carboxylic acid derivative of amide groups ($—CONH_2$—>$COOH$).

Included within the scope of the present invention are all stereoisomers, geometric isomers and tautomeric forms of the compounds of formula I, including compounds exhibiting more than one type of isomerism, and mixtures of one or more thereof. Also included are acid addition salts wherein the counterion is optically active, Compounds of the present invention can form acid addition salts, by reaction of the amino substituent of a compound of formula (Ia) or a compound of formula (Ib), with a suitable acid. As the salt form they may have solubility characteristics that are particularly suitable for a drug candidate, in addition to other desirable properties for a drug candidate.

Pharmaceutically acceptable salts of the compound of formula (Ia) or pharmaceutically acceptable salts of the compound formula (Ib), include the acid addition salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphthalenedisulfonate and xinofoate salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of a compound of formula (Ia) or pharmaceutically acceptable salts of a compound of formula (Ib) may be prepared by one or more of three methods:
 (i) by reacting a compound of formula (Ia) or a compound of formula (Ib) with a desired acid;
 (ii) by removing an acid- or base-labile protecting group from a suitable precursor of a compound of formula (Ia) or (Ib)
 (iii) by converting one salt of a compound of formula (Ia) or a compound of formula (Ib) to another by reaction with an appropriate acid or base or by means of a suitable ion exchange column.

The present invention also includes all pharmaceutically acceptable isotopically-labelled compounds of formula (Ia) or compounds of formula (Ib) wherein one or more atoms are replaced by atoms having the same atomic number, but an atomic mass or mass number different from the atomic mass or mass number which predominates in nature.

Isotopically-labelled compounds of formula (Ia) or compounds of formula (Ib) can generally be prepared by conventional techniques known to those skilled in the art or by processes analogous to those described in the accompanying Examples and Preparations using an appropriate isotopically-labelled reagent in place of the non-labelled reagent previously employed.

Certain isotopically-labelled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

As used herein, the term "5-LO mediated disease", or "5-LO-mediated disorder" or "5-LO-mediated condition" refers to any disease, disorder, or condition (particularly any pathological conditions), respectively, in which 5-LO plays a role, either by control of 5-LO itself, or by 5-LO causing leukotrienes to be released, or other like compounds whose production or action is exacerbated or secreted in response to 5-LO.

It has now been found that a compound of formula (Ia) or (Ib) or a pharmaceutically acceptable salt and solvate thereof is particularly useful for the treatment of a 5-LO mediated disease, disorder, or condition. Examples of 5-LO mediated diseases, disorders, or conditions, include, but are not limited to, allergic and non-allergic airway diseases, disorders, or conditions.

Examples of allergic and non-allergic airway diseases, disorders, or conditions include the diseases, disorders and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolitis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupous bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

Further examples of diseases, disorders, or conditions that can be treated with compounds of the present invention include those listed in Table I:

Table I (a) inflammation, including but not limited to smoke-induced airway inflammation and inflammation enhanced cough;
(b) arthritis, such as rheumatoid arthritis, spondyloarthropathies, systemic lupus erythematosus arthritis, juvenile arthritis, osteoarthritis, and gouty arthritis;
(c) neuroinflammation;
(d) pain (i.e., use of the compounds as analgesics), such as nociceptive or neuropathic pain;
(e) fever (i.e., use of the compounds as antipyretics);
(f) pulmonary sarcoisosis, and silicosis;
(g) cardiovascular diseases, such as atherosclerosis, myocardial infarction (such as post-myocardial infarction indication) thrombosis, congestive heart failure, cardiac reperfusion injury, and complications associated with hypertension and/or heart failure such as vascular organ damage;
(h) cardiomyopathy;
(i) stroke, such as ischemic and hemorrhagic stroke;
(j) ischemia, such as brain ischemia and ischemia resulting from cardiac/coronary bypass or ischemia induced myocardial injury;
(k) reperfusion injury including post-ischemic reperfusion injury;
(l) renal reperfusion injury;
(m) brain edema or brain injury;
(n) neurotrauma and brain trauma, such as closed head injury;
(o) neurodegenerative disorders;
(p) central nervous system disorders (these include, for example, disorders having an inflammatory or apoptotic component), such as Alzheimer's disease, Parkinson's disease, Huntington's Disease, amyotrophic lateral sclerosis, myasthenia gravis, spinal cord injury, and peripheral neuropathy;
(q) liver disease;
(r) hypercholesterolemia and dyslipidemias;
(s) gastrointestinal conditions including gastritis, gastric varices, inflammatory bowel disease, Crohn's disease, gastritis, irritable bowel syndrome, and ulcerative diseases including ulcerative colitis and gastric ulcer;
(t) nephritis;
(u) ophthalmic diseases, such as retinitis, retinopathies (such as diabetic retinopathy), uveitis, ocular photophobia, non-glaucomatous optic nerve atrophy, and age-related macular degeneration (ARMD) (such as ARMD-atrophic form);
(v) opthalmological conditions, such as corneal graft rejection, ocular neovascularization, retinal neovascularization (such as neovascularization following injury or infection) and retrolental fibroplasia;
(w) glaucoma, such as primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation, and corticosteroid-induced glaucoma;
(x) acute injury to the eye tissue and ocular traumas, such as post-traumatic glaucoma, traumatic optic neuropathy, and central retinal artery occlusion (CRAO);
(y) diabetes including type I diabetes and type II diabetes;
(z) diabetic nephropathy;
(aa) skin-related conditions, such as psoriasis, eczema, burns, dermatitis, keloid formation, scar tissue formation, scleroderma and angiogenic disorders;
(bb) viral and bacterial infections, such as sepsis, septic shock, gram negative sepsis, malaria, meningitis, opportunistic infections, cachexia secondary to infection or malignancy, cachexia secondary to acquired immune deficiency syndrome (AIDS), AIDS, ARC (AIDS related complex), pneumonia, herpes simplex infections, rhinovirus infections, and herpes virus;
(cc) myalgias due to infection;
(dd) influenza;
(ee) endotoxic shock;
(ff) toxic shock syndrome;
(gg) autoimmune disease, such as graft vs. host reaction and allograft rejections;
(hh) bone resorption diseases, such as osteoporosis;
(ii) multiple sclerosis;

(jj) disorders of the female reproductive system, such as endometriosis, menstrual cramps, vaginitis and candidiasis;
(kk) pathological, but non-malignant, conditions, such as haemangiomas (such as infantile haemangiomas), angiofibroma of the nasopharynx, and avascular necrosis of bone;
(mm) benign and malignant tumors/neoplasia including cancer of any kind, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer, skin cancer such as squamous cell and basal cell cancers, prostate cancer, renal cell carcinoma, Hodgkin's disease, and other known cancers that affect epithelial cells throughout the body;
(nn) systemic lupus erthrematosis (SLE);
(oo) angiogenesis including neoplasia;
(pp) metastasis;
(qq) a fibrotic disease;
(rr) hemorrhage;
(ss) coagulation;
(tt) acute phase responses like those seen with infections and sepsis and during shock (e.g.,
(uu) septic shock, hemodynamic shock, etc.);
(vv) anorexia;
(ww) mycobacterial infection;
(xx) pseudorabies;
(yy) rhinotracheitis;
(zz) HIV;
(aaa) sarcoidosis;
(bbb) herpes virus, including herpes simplex virus type-1 (HSV-1), herpes simplex virus type-2 (HSV-2);
(ccc) cytomegalovirus (CMV);
(ddd) varicella-zoster virus (VZV);
(eee) Epstein-Barr virus;
(fff) human herpesvirus-6 (HHV-6);
(ggg) human herpesvirus-7 (HHV-7), human herpesvirus-8 (HHV-8);
(hhh) myogenesis;
(iii) mucin overproduction, and/or mucus hypersecretion;
(jjj) allergy, including allergic rhinitis;
(kkk) tissue destruction;
(lll) signs and symptoms such as breathless cough;
(mmm) disorders of the blood including aplastic anemia;
(nnn) spondyloarthropathies including lumbar spondylanhrosis and lumbar spondylarthrosis;
(ooo) disorders of the male reproductive system;
(ppp) headache pain including migraine headache pain, sinus headache pain, and tension headache pain;
(qqq) dental pain;
(rrr) rheumatic fever;
(sss) connective tissue injuries or disorders;
(ttt) obesity;
(uuu) pulmonary disorders and diseases (e.g., hyperoxic alveolar injury);
(vvv) a kidney stone;
(www) wound healing;
(xxx) a minor injury;
(yyy) radiation damage;
(zzz) bursitis;
(aaaa) vascular diseases;
(bbbb) pulmonary edema;
(cccc) conjunctivitis;
(dddd) tendinitis;
(eeee) cortical dementias;
(ffff) gingivitis;
(gggg) swelling occurring after injury;
(hhhh) periarteritis nodosa;
(iiii) thyroiditis;
(kkkk) polymyositis;
(llll) Behcet's syndrome;
(mmmm) nephritic syndrome; and
(nnnn) hypersensitivity.

As said in Table I (d) above, the compounds of formula (I), are thought to be useful in the treatment of a range of pain-related disorders.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardial infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

A further embodiment of the invention is the use of a compound of formula (Ia) or (Ib), or pharmaceutically acceptable salts and solvates thereof, in the manufacture of a medicament useful in the treatment of a 5-LO mediated disease, disorder, or condition, preferably but not exclusively those selected from the group consisting of:
asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolitis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupous bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

Besides being useful for human treatment, compounds of the present invention are also useful for veterinary treatment of companion animals, exotic animals and farm animals, including mammals for the treatment of a 5-LO mediated disease, disorder or condition disclosed in the present disclosure. As a matter of example, the compounds of the present invention are useful for the treatment of a 5-LO mediated disease, disorder, or condition in a horse, dog, or cat.

In another embodiment of the present invention, a compound of the invention can also be used in a combination with one or more additional therapeutic agents. Such a combination, for treating a 5-LO mediated disease can be co-administered to a patient to obtain some particularly desired therapeutic end result such as the treatment of any one or combination thereof, but not limited to, a disease, disorder, or condition listed in Table I.

As used herein, the terms "co-administration", "co-administered" and "in combination with", referring to the compounds of the invention and one or more other therapeutic agents, is intended to mean, and does refer to and include the following:

simultaneous administration of such combination of compound(s) of the invention) and therapeutic agent(s) to a patient in need of treatment, when such components are formulated together into a single dosage form which releases said components at substantially the same time to said patient, substantially simultaneous administration of such combination of compound(s) of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of the invention and therapeutic agent(s) to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

Suitable examples of other therapeutic agents which may be used in combination with a compound of the invention, or pharmaceutically acceptable salts, solvates or compositions thereof, include those of Table II below. Among the numerous therapeutic agents that may be co-administered with the compounds of this invention, are one or more 5-LO inhibitors known in the art.

Table II (a) 5-lipoxygenase activating protein (FLAP) antagonists;
(b) Leukotriene antagonists (LTRAs) including antagonists of $LTB_4$, $LTC_4$, $LTD_4$, and $LTE_4$;
(c) Histamine receptor antagonists including H1 and H3 antagonists;
(d) $\alpha_1$- and $\alpha_2$-adrenoceptor agonist vasoconstrictor sympathomimetic agents for decongestant use;
(e) muscarinic M3 receptor antagonists or anticholinergic agents;
(f) PDE inhibitors, e.g. PDE3, PDE4 and PDE5 inhibitors, such as theophylline;
(g) Sodium cromoglicate;
(h) COX inhibitors both non-selective and selective COX-1 or COX-2 inhibitors (such as NSAIDs);
(i) glucocorticosteroids or DAGR (dissociated agonists of the corticoid receptor);
(j) Monoclonal antibodies active against endogenous inflammatory entities;
(k) β2 agonists, including long-acting β2 agonists;
(l) Integrin antagonists;
(m) Adhesion molecule inhibitors including VLA-4 antagonists;
(n) $Kinin-B_1$- and $B_2$-receptor antagonists;
(o) Immunosuppressive agents, including inhibitors of the IgE pathway, and cyclosporin;
(p) Inhibitors of matrix metalloproteases (MMPs), e.g., MMP9, and MMP12;
(q) Tachykinin $NK_1$, $NK_2$ and $NK_3$ receptor antagonists;
(r) Protease inhibitors, e.g., elastase;
(s) Adenosine A2a receptor agonists and A2b antagonists;

(t) Inhibitors of urokinase;
(u) Compounds that act on dopamine receptors, e.g. D2 agonists;
(v) Modulators of the NFκB pathway, e.g. IKK inhibitors;
(w) modulators of cytokine signaling pathways such as syk kinase, JAK kinase inhibitors, p38 kinase, EGF-R or MK-2;
(x) Agents that can be classed as mucolytics or anti-tussive, and mucokinetics;
(y) Antibiotics;
(z) Antivirals;
(aa) Vaccines;
(bb) Chemokines;
(cc) Epithelial sodium channel (ENaC) blockers or Epithelial sodium channel (ENaC) inhibitors;
(dd) P2Y2 Agonists and other Nucleotide receptor agonists;
(ee) Inhibitors of thromboxane;
(ff) Niacin;
(gg) Inhibitors of $PGD_2$ synthesis and $PGD_2$ receptors (DP1 and DP2/CRTH2);
(hh) Adhesion factors including VLAM, ICAM, and ELAM;
(ii) Statins or other treatments for hypercholesterolemia; cholesterol and lipid absorption inhibitors (e.g., nicotinic acid, niacin, cholesterol transporters).

The additional therapeutic agent can be administered per se, in a mixture with one or more other compounds of the invention, or in the form of pharmaceutical preparation, which, as active constituent contains an efficacious dose of at least one compound of the invention, in addition to customary pharmaceutically innocuous excipients. "additive" is comprised within the meaning of "excipient" (see below).

One embodiment of the invention is therefore the use of a compound of formula (Ia) or (Ib) or a pharmaceutically acceptable salt and solvate thereof, in combination with any compound listed in Table II for the treatment of a 5-LO mediated disease, disorder, or condition. According to another embodiment of the invention, said 5-LO mediated diseases, disorder or condition is selected from those listed in Table I.

A further embodiment of the invention is the use of a compound of formula (Ia) or (Ib), or pharmaceutically acceptable salts and solvates thereof, in combination with any compound listed in Table II, in the manufacture of a medicament for the treatment of any disorder listed in Table I.

In one embodiment, a method of treating pain is provided. In this embodiment, the method comprises administering to a subject in need thereof a therapeutically effective amount of a compound of Formula (Ia) or I(b), alone or in combination with another active agent. Pain may include nociceptive or neuropathic pain. The additional active agent may include a GABA analog such as gabapentin or pregabalin, an opiod such as morphine, a non-steroidal anti-inflammatory (NSAID), a COX-2 inhibitor, a steroid or a modulator of the eicosanoid pathway.

In one embodiment, a method of treating pathological hepatic conditions in a subject in need thereof is provided. In this embodiment, the method comprises administering to the subject a compound of Formula (Ia) or I(b), alone or in combination with another active agent. Hepatic conditions may include, for example, cirrhosis of the liver, fatty liver, hepatitis, nonalcoholic steatohepatitis (NASH), liver fibrosis, benign hepatic tumors and the like. Accordingly, additional active agents, such as, for example, antivirals, Peroxisome proliferator-activated receptor (PPAR)-γ ligands such as thiazolidinediones, transforming growth factor β inhibitors and the like may be co-administered with compounds of the present invention.

In one embodiment, a method of treating osteoporosis is provided. In this embodiment, the method comprises administering to a subject in need thereof an effective amount of a compound of Formula (Ia) or I(b), alone or in combination with another active agent.

In one embodiment, a method of treating metabolic syndrome is provided. In this embodiment, the method comprises administering to a subject in need thereof a compound of Formula (Ia) or I(b), alone or in combination with another active agent.

In one embodiment, a method of treating pathologically high cholesterol in a subject in need thereof is provided. In this embodiment, the method comprises administering to the subject a therapeutically effective amount of a compound of Formula (Ia) or I(b), alone or in combination with another active agent. Accordingly, cholesterol modifying or modulating agents may be administered in combination with a compound of Formula (I), Formula (Ia) or Formula I(b) of the present invention. Such cholesterol modifying or modulating agents include but are not limited to, HMG-CoA reductase inhibitors (or "statins") such as lovastatin (Mevacor), atorvastatin (Lipitor), pravastatin (Pravachol), and simvastatin (Zocor); squalene monooxygenase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; and LDL (low density lipoprotein) receptor inducers, for example.

In one embodiment, a method of treating a cardiovascular condition in a subject in need thereof is provided. In this embodiment, the method comprises administering to a subject an effective amount of a compound of Formula (Ia) or I(b), alone or in combination with another active agent. Such additional active agents may include a mineralocorticoid receptor modulator, such as eplernone or spironolactone, an angiotensin converting enzyme (ACE) inhibitor such as quinapril (Accupril) or fosinopril (Monopril); an angiotensin receptor antagonist; vitamin B-6 (also known as pyridoxine) and the pharmaceutically acceptable salts thereof such as the HCl salt; vitamin B-12 (also known as cyancobalamin); β-adrenergic receptor blockers; folic acid or a pharmaceutically acceptable salt or ester thereof such as the sodium salt and the methylglucamine salt; and anti-oxidant vitamins such as vitamin C and E and beta carotene.

In one embodiment, a method of treating a neoplasia in a subject in need thereof is provided. In this embodiment, the method comprises administering to a subject an effective amount of a compound of Formula (Ia) or I(b), alone or in combination with another active agent. Accordingly, additional active agents such as Ipha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin 1, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (triptorelin), or an omega-3 fatty acid may be administered with the compounds of the present invention.

One specific example of a useful combination therapy according to the present invention, is a combination comprising a compound of formula (Ia) or (Ib) or pharmaceutically acceptable salts and solvates thereof, with a glucocorticosteroid (or a DAGR (dissociated agonist of the glucocorticoid receptor). Examples of Glucocorticosteroids include, but are not limited to, prednisone, prednisolone, flunisolide, triamcinolone acetonide, bechlometasone dipropionate, budesonide, fluticasone propionate, ciclesonide and mometasone furoate. Examples of DAGR compounds useful in combination with compounds of the present invention include, but are not limited to, those described in international patent application publications WO/2000/06522 and WO/2004/005229.

Another specific example of a useful combination therapy according to the present invention, is a combination comprising a compound of formula (Ia) or (Ib) or pharmaceutically acceptable salts and solvates thereof, with a COX inhibitor, either non-selective or selective COX-1 or COX-2 inhibitors (NSAIDs) such as ibuprofen or celecoxib, or a pharmaceutically acceptable salt thereof.

Another specific example of a useful combination therapy according to the present invention, is a combination comprising a compound of formula (Ia) or (Ib) or pharmaceutically acceptable salts and solvates thereof, with a β2 agonist.

Examples of β2 agonists include, but are not limited to, salmeterol, formeterol, QAB-149 and carmoterol.

Another specific example of a useful combination therapy according to the present invention, is a combination comprising a compound of formula (Ia) or (Ib) or pharmaceutically acceptable salts and solvates thereof, with a muscarinic M3 receptor antagonist or an anticholinergic agent. Examples of M3 receptor antagonists include, but are not limited to, tiotropium, ipratropium, oxitropium, pirenzepine and telenzepine.

Another specific example of a useful combination therapy according to the present invention, is a combination comprising a compound of formula (Ia) or (Ib) or pharmaceutically acceptable salts and solvates thereof, with a histamine receptor antagonist, a examples of which includes an H1 and an H3 antagonist.

Inasmuch as it may desirable to administer active compounds in combination, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula I in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of a compound of the invention is typically in the range of 0.01 mg to 2000 mg depending, of course, on the mode of administration. In another embodiment of the present invention, the total daily dose of a compound of the invention is typically in the range of 0.1 mg to 500 mg. In yet another embodiment of the present invention, the total daily dose of a compound of the invention is typically in the range of 1 mg to 300 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

In the case of aerosols, the dosage unit is determined by means of a valve which delivers a metered amount. Units in accordance with the invention are typically arranged to administer a metered dose or "puff" containing from 0.001 mg to 10 mg of a compound of the invention. The overall daily dose will typically be in the range 0.001 mg to 40 mg which may be administered in a single dose or, more usually, as divided doses throughout the day.

According to an embodiment of the invention, there is thus provided a pharmaceutical composition comprising a compound of formula (Ia) or (Ib) or a pharmaceutically acceptable salt and solvate thereof, and a pharmaceutically acceptable excipient.

The term 'excipient' is used herein to describe any ingredient other than compound(s) of the invention. The choice of excipient will to a large extent depend on factors such as the particular mode of administration, the effect of the excipient on solubility and stability, and the nature of the dosage form. The term "excipient" encompasses diluents, carriers and adjuvants.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, dispersions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. In one embodiment, a liquid formulation is an extemporarily prepared oral suspension of micronized compounds of the invention, optionally combined with soluble macromolecular entities, such as cyclodextrins and suitable derivatives thereof, as defined below.

Compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of the invention, a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

The compounds of the invention may also be administered topically to the skin or mucosa, that is, dermally or transdermally.

The compounds of the invention can also be administered intranasally, typically in the form of a dry powder (either alone, as a mixture, for example, in a dry blend with lactose, or as a mixed component particle, for example, mixed with phospholipids, such as phosphatidylcholine) from an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Capsules (made, for example, from gelatin or hydroxypropylmethylcellulose), blisters and cartridges for use in an insufflator may be formulated to contain a powder mix of a compound of the invention, a suitable powder base such as lactose or starch and a performance modifier such as l-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of a compound of the invention per actuation and the actuation volume may vary from 1 µl to 100 µl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration.

Formulations for intranasal administration may be formulated to be immediate and/or modified release using, for example, PGLA. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. A suitable cyclodextrin is sulfobutylethyl cyclodextrin (SBECD). A preferred cyclodextrin is hydroxylpropyl β-cyclodextrin HPBCD (CAS number: 128446-35-5).

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

According to a preferred embodiment, the compounds of the present invention are particularly suitable for administration via the oral route.

The compounds of formula (I) may be prepared, in a variety of ways by one skilled in the art. The following routes illustrate such ways of preparing these compounds; the person of ordinary skill in the art will appreciate that other routes may be equally as practicable.

A compound of formula (Ia) may be prepared according to the following process, where the term 'tips' means triisopropylsilyl:

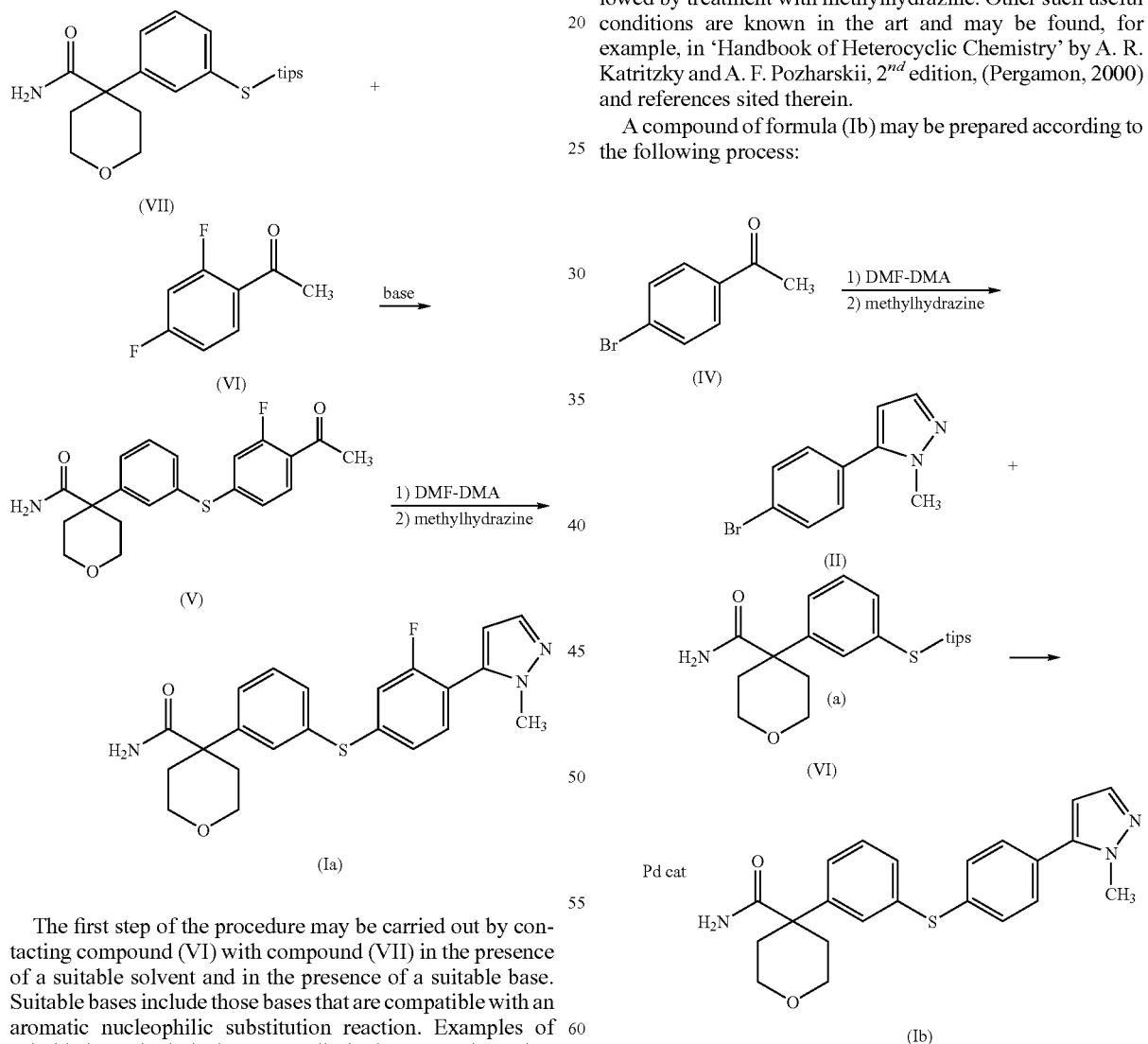

The first step of the procedure may be carried out by contacting compound (VI) with compound (VII) in the presence of a suitable solvent and in the presence of a suitable base. Suitable bases include those bases that are compatible with an aromatic nucleophilic substitution reaction. Examples of suitable bases include, but are not limited to, potassium t-butoxide and sodium hydride. Examples of suitable solvents for this reaction include, but are not limited to, toluene, tetrahydrofuran, dioxane, and dimethoxyethane. Additionally, another suitable reagent may be added to remove the protecting group. Examples of suitable reagents that may be added to remove the protecting group include, but are not limited to, tetrabutylammonium fluoride, cesium fluoride and small amount of water. The reaction may be carried out at a variety of suitable temperatures. Typically, the reaction may be carried out at a temperature of about 24° C. to about 110° C., preferably at a temperature of about 85° C. to about 95° C. More preferably, the reaction may be carried out at a temperature of about 90° C. The reaction is carried out for a time sufficient to allow the formation of an acceptable yield of the product. Typically, the reaction is carried out for from about 2 hours to about 10 hours. Preferably the reaction is carried out for about 4 hours.

The second step of the reaction may be carried out by contacting compound (V) with a suitable reagent and suitable conditions to facilitate pyrazole formation. It may be desirable to carry out the reaction under such conditions to minimize the occurrence of the regioisomeric pyrazole. One useful example of reagents that may be used in this particular reaction is N,N'-dimethylformamide dimethyl acetal followed by treatment with methylhydrazine. Other such useful conditions are known in the art and may be found, for example, in 'Handbook of Heterocyclic Chemistry' by A. R. Katritzky and A. F. Pozharskii, $2^{nd}$ edition, (Pergamon, 2000) and references sited therein.

A compound of formula (Ib) may be prepared according to the following process:

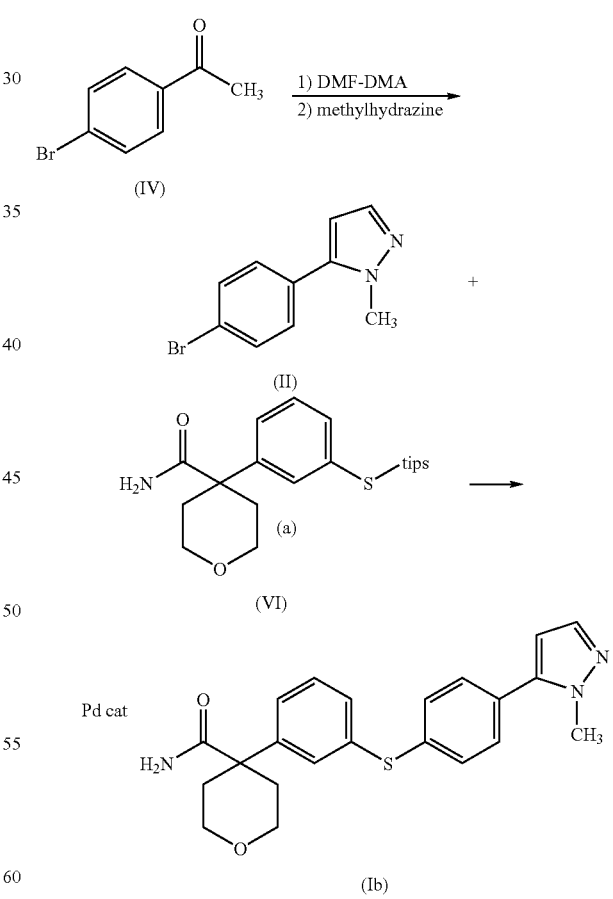

The first step of the procedure may be carried out under conditions similar to those described above for the second step of (Ia). For example, compound (IV) may be contacted with N,N'-dimethylformamide dimethyl acetal followed by treatment with methylhydrazine. Two alternatives suitable routes to synthesize compound (II) are disclosed in the Examples of the present Application. The first step is believed to proceed via the formation of an intermediate enamine of formula (III):

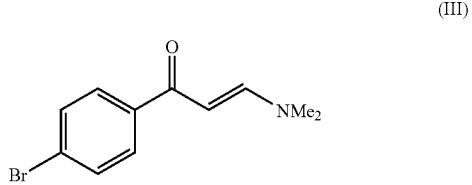

(III)

The formation of intermediate (III) can be followed for example via HPLC.

The second step of this reaction is carried out in the presence of a suitable catalyst. An example of a suitable catalyst for this coupling reaction is a palladium catalyst. Specific examples of suitable catalysts that may be used for this reaction include tetrakis triphenylphosphine palladium, Tris(dibenzylideneacetone)-dipalladium(0), palladium acetate, or dichloro-(1,2-bis-diphenylphosphino-ethane)-palladium (II).

The second step of this reaction is also carried out in the presence of a suitable solvent. Examples of suitable solvents that may be used to carry out this reaction include isopropanol, methanol, or dioxane. For scale-up versions, 2-methyltetrahydrofuran can be used.

A variety of suitable bases may also be used in this reaction. Examples of suitable bases that may be used in this reaction include potassium t-butoxide, cesium carbonate, or potassium phosphate. For scale-up versions, sodium methoxide can be used.

Additional suitable reagents may also be added to facilitate the reaction. Examples of suitable additional reagents that may be added to facilitate the reaction include cesium fluoride, water, tetraethylammonium chloride, or tetrabutylammonium fluoride.

A suitable additional ligand may also be added to the reaction. Examples of suitable additional ligands that may be added to the reaction include, for instance, Bis(2-diphenylphosphinophenyl)ether, 1,1'-Bis(diphenyl-phosphino)ferrocene, or 9,9-dimethyl-4,5-bis(diphenylphosphino)xanthene.

This reaction may be carried out at a variety of suitable temperatures. Typically, the reaction may be carried out at a temperature of about 24° C. to about 110° C., preferably at the reflux temperature of the solvent.

Purification of product (Ib) from crude reaction product can be performed as described in the Examples of the present Application.

A scale-up version of the second step to arrive at compound (Ib) is described in the Examples of the present Application.

It will be appreciated by those skilled in the art that it may be necessary or desirable at any stage in the synthesis of compounds of formula (Ia) or (Ib) to protect one or more sensitive groups in the molecule so as to prevent undesirable side reactions. The protecting groups used in the preparation of compounds of formula (Ia) or (Ib) may be used in a conventional manner. See, for example, those described in 'Protective Groups in Organic Synthesis' by Theodora W Green and Peter G M Wuts, third edition, (John Wiley and Sons, 1999) in particular chapter 2, pages 17-245 ("Protection for the Hydroxyl Group").

The starting compounds used in the synthesis of compounds of formula (Ia) or (Ib) of the present invention, as illustrated on the preceding page, are either commercially available or can be prepared as described in the Examples of the present Application.

Also within the scope of the invention are novel intermediates as herein defined, all pharmaceutically acceptable salts and complexes thereof and all solvates and complexes of pharmaceutically acceptable salts thereof as defined herein for compounds of formula (Ia) or (Ib).

EXAMPLES AND PREPARATIONS

In another embodiment of the invention, there is provided a process for making a compound of formula (Ia) or (Ib), and the description related to the processes, which comprises the steps as follows:

Example 1

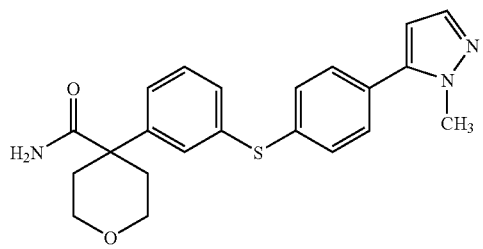

4-(3-{[4-(1-methyl-1H-pyrazol-5-yl)phenyl]thio}phenyl)tetrahydro-2H-pyran-4 carboxamide Step 1: Preparation of 4-(3-bromophenyl)-tetrahydro-2H-pyran-4-carboxamide 4-(3-bromophenyl)tetrahydro-2H-pyran-4-carbonitrile made by the procedures described in EP 108114 (1.05 kg, 3.95 mole) was stirred in 98% $H_2SO_4$ (3.00 L) at room temperature for about 40 h. The mixture was then poured onto ice and the very fine suspension was filtered and washed with $H_2O$ thoroughly until pH of wash is neutral. The white solid was washed with hexanes and was then dried in vacuo at 35-40° C. to give 1119 g (99.8% yield) of product in 99.9% purity. LC/MS: 5%-100% CH3CN:H20-0.01% TFA gradient over 10 minutes: 4.68 min. (M+H)$^+$. $^1$H NMR (400 MHz, DMSO-d$_6$) δ ppm 7.50-7.49 (m, 1H), 7.43-7.40 (m, 1H), 7.36-7.30 (m, 1H), 7.27 (d, J=7.92 Hz, 1H) 7.06 (s, 1H), 5.00 (brs, 1H) 3.71 (dt, J=11.7, 3.7 Hz, 2H), 3.42 (t, J=10.7 Hz, 2H), 2.38 (d, J=13.6 Hz, 2H), 1.75 (td, J=12.2, 4.3 Hz, 2H).

Step 2: Preparation of 4-(3-(triisopropylsilylthio)phenyl)-tetrahydro-2H-pyran-4-carboxamide Alternative 1

4-(3-Bromophenyl)-tetrahydro-2H-pyran-4-carboxamide prepared in step 1 (300 g (1.06 mole), sodium tert-butoxide (122 g, 1.27 mole), Pd(OAc)$_2$ (4.74 g 0.0211 mole) and DIPPF (1,1-bis(diisopropylphosphino)ferrocene) (10.6 g 0.0253 mole) were placed in a flask which was evacuated and filled with N$_2$ 3 times. Anhydrous dioxane (2.3 L) was added and the mixture was stirred at room temperature for 1 h. To the mixture was added triisopropylsilane thiol (221 g 1.16 mole)

and the resulting mixture was heated to reflux. Reflux was stopped after 1 h and the mixture was allowed to cool to room temperature. The mixture was then poured into ethyl acetate (7 L) which was then washed with H₂O (2×4 L) and brine (2 L). The combined aqueous washes were back extracted with ethyl acetate (3 L) which was then washed with H₂O (2×2 L) and brine (1 L). The combined organic layers were dried over MgSO₄, filtered and concentrated to dryness. Ethyl acetate (0.5 L) was added to the solid and the mixture was stirred on the rotary evaporator to give a fine suspension. Hexanes (1.5 L) was then added and the suspension was allowed to stand for 1 hour. The solid was filtered, washed with 1:1 ethyl acetate-hexanes (1 L) and then hexanes. The resulting brown solid was dried in vacuo to give 334 g (80% yield) of the product in 99% purity. A second crop was obtained from the filtrate which was washed as before and dried to give an additional 15 g product for a total yield of 84%. LC/MS: 5%-100% CH3CN:H20-0.01% TFA gradient over 10 minutes: 9.35 min. 394.1 (M+H)⁺. ¹H NMR (400 MHz, CDCl₃) δ ppm 7.52-7.51 (m, 1H) 7.42-7.39 (m, 1H), 7.22-7.21 (m, 2H), 5.35 (brs, 1H), 5.13 (brs, 1H) 3.78-3.75 (m, 4H) 2.36-2.32 (m, 2H), 2.06-2.00 (m, 2H), 1.27-1.16 (m, 3H), 1.05 (d, J=7.25 Hz, 18H).

Step 2: Preparation of 4-(3-(triisopropylsilylthio) phenyl)-tetrahydro-2H-pyran-4-carboxamide Alternative 2

Purge a 3-neck flask (overhead stirrer, nitrogen inlet, serum cap) with nitrogen. Add 4-(3-Bromophenyl)-tetrahydro-2H-pyran-4-carboxamide prepared in step 1 (10 g, 0.03519 mole). Add sodium t-butoxide (4.1 g, 0.04223 moles). Add anhydrous toluene. Toluene should be as dry as possible, <0.01% water by KF is sufficient. Initiate stirring. Purge the reaction mixture with 4 vacuum/nitrogen purge cycles, maintaining 60 torr vacuum for 30 seconds with each cycle. Add the thiol (9.1 g, 0.04223 moles) assuring that oxygen is not introduced into the vessel. Heat to 75° C. Add PdCl2(diphenyl-phosphino ferrocene) (0.258 g, 0.00035 moles). Continue heating to reflux (reaction temperature about 107° C.) for a minimum of 1 hour. The mixture should reach reflux within 30 minutes.

Cool the reaction mixture to 25° C. Add ethyl acetate (300 mL, 30 mL/g) and stir the resulting suspension for 30 min. Filter the suspension through celite (30 g). Rinse the celite with ethyl acetate for rinse (100 mL, of product to be rinsed), combining filtrates. Concentrate the filtrate via vacuum distillation at 70 torr at 30° C. until 80% of the filtrate volume has been removed. Add hexane (200 mL, 20 mL/g of product to be crystallized) for crystallization to the slurry over 5 minutes. Stir and cool the mixture to 5° C. Maintain the mixture at 5° C. for a minimum of 1 hour. Isolate product by filtration. Rinse the cake with hexane (100 mL, of product to be rinsed). Dry the cake on the filter to LOD of no more than 5%. Dry the solid at 45-50° C. under vacuum to an LOD of no more than 1.5%. Yield 12 grams (85% yield).

Any mL/g amount indicated above is referred to grams of bromo carboxamide.

Step 3: Preparation of 5-(4-bromophenyl)-1-methyl-1H-pyrazole

Alternative 1

A N,N'-dimethylformamide (15 mL) solution of 4-bromoacetophenone (10.60 g, 53.25 mmols) and N,N'-dimethylformamide dimethyl acetal (2.5 equivalents) was heated at 125 degrees Celcius for 3 hours. The dark red solution was cooled to room temperature. The volatiles were removed by rotary evaporation providing a red viscous oil. To this substance was added anhydrous N,N'-dimethylformamide (15 mL) and methyl hydrazine (7.6 g, 160 mmols, 3 equivalents). The mixture was stirred at room temperature for 1 hour and then heated at 75 degrees Celcius for 4 hours. The volatiles were removed by rotary evaporation and the crude residue was taken up in a small volume of methylene chloride. This red solution was applied to a cartridge of silica gel. The cartridge was eluted with a 20:80 mixture of ethyl acetate and hexanes, respectively. The appropriate fractions were combined and concentrated to produce 12.5 g of a white solid.

¹H NMR (400 MHz, CHLOROFORM-d) δ ppm 3.87-3.95 (m, J=2.22 Hz, 3H) 6.29-6.36 (m, 1H) 7.31 (dd, J=8.36 Hz, 2H) 7.52-7.56 (m, 1H) 7.62 (dd, J=2.05 Hz, 2H).

Step 3: Preparation of 5-(4-bromophenyl)-1-methyl-1H-pyrazole

Alternative 2

4-bromoacetophenone (20.0 g; 0.10 mole) and N,N-dimethylformamide dimethylacetal (28.5 mL; 0.20 mole) were mixed together in DMF (12 mL) and heated to 110° C. for 4 hours. The methanol and water that were generated during the reaction were distilled (6.2 mL). The mixture was cooled to 25° C. Methyl t-butyl ether (100 mL) and methylhydrazine (21.2 mL; 0.40 moles) were added and the mixture was stirred over night. The reaction mixture was washed with 1 M aqueous ammonium chloride (3×40 mL) and water (40 mL). The organic phase was dried by azeotropic distillation using a Dean-Stark apparatus. As an alternative to distillation, the solution was dried through an anhydrous magnesium sulfate cartridge. The solution was filtered through a silica gel cartridge (60 g). The product was flushed from the cartridge with methyl t-butyl ether. The fraction(s) containing product were combined and concentrated to about 70 mL by distillation. Heptane (120 mL) was added and distillation was continued until the pot temperature reached 98.4° C. About 100 mL of distillate was collected. The mixture was cooled to 40° C. The mixture was seeded and the temperature was maintained at 40° C. for 30 minutes while crystallization was initiated. The mixture was slowly chilled to 0° C. over 90 minutes. The mixture was held at 0° C. for 30 minutes. The mixture was filtered and the solid was washed (3×) with chilled (0° C.) heptane. The solid was dried on the filter. A cream-colored, crystalline solid (16.3 g; 68% yield) was obtained. The NMR data of the title compound are as per alternative 1.

Step 4: Preparation of 4-(3-{[4-(1-methyl-1H-pyrazol-5-yl)phenyl]thio]phenyl) tetrahydro-2H-pyran-4-carboxamide A mixture of 5-(4-bromophenyl)-1-methyl-1H-pyrazole (0.50 g, 2.10 mmols,), 4-{3-[(tri-isopropylsilyl)thio] phenyl}tetrahydro-2H-pyran-4-carboxamide (0.83 g, 2.10 mmols), Tetrakis(triphenylphosphine)palladium(0) (243 mg, 0.10 equivalents), bis[(2-diphenyl-phosphino)]phenyl ether (113 mg, 0.10 equivalents), and 1.0 M potassium tert-butoxide in THF (6.3 mmols, 3 equivalents) in iPrOH (15 mL) that contained 5% water was heated for 4 hours at 90 degrees Celcius in an atmosphere of nitrogen. The reaction mixture was cooled to room temperature and 7 mL of 1N HCl was added. The product was precipitated by the addition of water (30 mL). The precipitate was collected by suction filtration and washed with water (2×20 mL) and cold ethyl ether (4×20 mL). The tan brown solid was dissolved in a small volume of methylene chloride containing 1% methanol and applied to a 140 g cartridge of silica gel. The cartridge was eluted with an acetone:hexane gradient. The appropriate fractions were concentrated and triturated with methanol to produce a white solid (710 mg) as product. $^1$H NMR (400 MHz, DMSO-d$_6$) δ ppm 1.75-1.84 (m, 3H) 2.40 (d, J=13.54 Hz, 3H) 3.43-3.51 (m, 1H) 3.72 (d, J=11.34 Hz, 3H) 3.84 (s, 3H) 6.40 (d, J=1.46 Hz, 1H) 7.02 (s, 1H) 7.22-7.30 (m, 2H) 7.34 (d, J=8.05 Hz, 1H) 7.38-7.43 (m, 2H) 7.45-7.52 (m, 3H). HRMS calc M+H, 394.1589, found 394.1630.

Step 4: Preparation of 4-(3-{[4-(1-methyl-1H-pyrazol-5-yl)phenyl]thio]phenyl) tetrahydro-2H-pyran-4-carboxamide Scale-Up Alternative 4-{3-[(tri-isopropylsilyl)thio]phenyl}tetrahydro-2H-pyran-4-carboxamide (200 g, 0.51 moles), 5-(4-bromophenyl)-1-methyl-1H-pyrazole (126 g, 0.53 moles), and 2-methyltetrahydrofuran (2,000 mL, 10 mL/g of tips carboxamide) were put into the reactor and sparged with nitrogen while heating to 60° C. The sodium methoxide (244.0 mL, 1.07 moles, added as sodium methoxide in methanol solution 25% w/w) was added to the reactor and sparging was continued for another 30 minutes. PdCl$_2$DPPF (3.7 g, 0.005 moles) was added to the reactor and the mixture was heated to 70° C. Once the amount of tips carboxamide was less than 1% of starting amount, the mixture was cooled to 0° C. The mixture was held at 0° C. for one hour. The mixture was filtered and the solid was washed with 2-methyltetrahydrofuran (3×2.5 mL/g). The solid was dried on the filter. The solid was returned to a clean reactor and triturated with water (2,000 mL, 10 mL/g) for two hours at 20° C. The mixture was filtered and the solid was washed with water (2,000 mL, 2×5 mL/g). The solid was dried on the filter. The solid was returned to a clean reactor with the Si-thiol (90.0 g, 0.5 g/g) and THF (about 12.8 L, 70 mL/g). The mixture was heated to 60-65° C. and held for two hours. The mixture was cooled to 25° C. and filtered. The Si-thiol was washed with THF (about 0.9 L, 5 mL/g). The solution was distilled to a concentration of 10 mL/g. The mixture was cooled to 25° C. and hexanes (422.5 mL, 5 mL/g) was added. The mixture was filtered and the solid was washed with hexanes (422.5 mL, 5 mL/g). The solid was dried in a vacuum oven at 70° C.

For 2-methyltetrahydrofuran and water, mL/g are referred to grams of tips carboxamide. For Si-thiol, tetrahydrofuran and hexanes, mL/g are referred to grams of title compound.

Step 5: Purification of 4-(3-{[4-(1-methyl-1H-pyrazol-5-yl)phenyl]thio]phenyl) tetrahydro-2H-pyran-4-carboxamide Crude title compound (181.0 g, 1.0 eq.) obtained from step 4, scale-up version, was returned to a clean reactor with Si-thiol (0.5 g/g of title compound) and THF (75 mL/g of title compound). The mixture was heated to 60-65° C. and held overnight. The mixture was cooled to 25° C. and filtered. The Si-thiol was washed with THF (5 mL/g of title compound). The solution was distilled to a concentration of 10 mL/g. Product may cake on reactor wall during the distillation. The mixture was cooled to 25° C. Hexanes (5 mL/g of title compound) was added and the mixture was held for 30 minutes. The mixture was filtered and the solid was dried on the filter. The reactor was rinsed with methanol to remove residual THF. The solid was returned to the reactor with methanol (20 mL/g of title compound). The mixture was heated to reflux and held over night. The mixture was cooled to 20° C. and held for 2 hours. The mixture was filtered. The solid was dried in a vacuum oven at 70° C. 162 g of purified title compound was obtained (85% yield). The NMR data of the title compound are as per Step 4.

Any mL/g amount indicated above is referred to grams of crude title compound.

Example 2

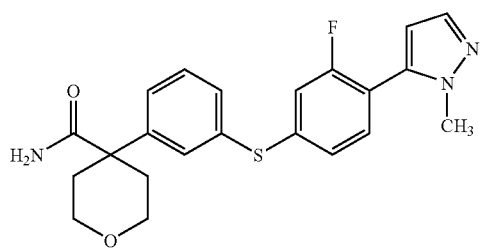

4-(3-{[3-fluoro-4-(1-methyl-1H-pyrazol-5-yl)phenyl]thio}phenyl)tetrahydro-2H-pyran-4-carboxamide Step 1: Preparation of 4-{3-[(4-acetyl-3-fluorophenyl)thio]phenyl}tetrahydro-2H-pyran-4-carboxamide 2,4-Difluoroacetophenone (0.40 g, 2.54 mmols), 4-{3-[(triisopropylsilyl)thio]phenyl}-tetra-hydro-2H-pyran-4-carboxamide (1.0 g, 2.54 mmols), tetrabutylammonium fluoride (0.66 g, 2.54 mmols), and potassium tert-butoxide (1.0 M in THF, 2.54 ml, 2.54 mmols) were added to anhydrous toluene (10 ml). The mixture was warmed to 90 degrees Celcius and stirred for 4 hours. After cooling to room temperature, ethyl acetate was added (100 ml) along with 1.0 N HCl (6 ml). The mixture was then stirred for 30 minutes and a beige precipitate was collected by suction filtration. The crude product was purified further on silica gel eluting with a 70:30 mixture of methylene chloride and acetone. The appropriate fractions were concentrated to a light brown solid, (0.61 g, 64%).

Step 2: Preparation of 4-(3-{[3-fluoro-4-(1-methyl-1H-pyrazol-5-yl)phenyl]thio}phenyl)tetrahydro-2H-pyran-4-carboxamide 4-{(3-[(4-acetyl-3-fluorophenyl)thio]phenyl}tetrahydro-2H-pyran-4-carboxamide (650 mg, 1.74 mmols) was added to anhydrous N,N'-dimethylformamide (5 ml). Then N,N'-dimethylformamide dimethyl acetal was added (1.03 g, 8.7 mmols, 5.0 equivalents) and the solution was heated at 100 degrees Celcius for four hours. The volatiles were evaporated under reduced pressure and the red residue was dissolved in anhydrous N,N'-dimethylformamide (5 ml). This solution was cooled to 0 degrees Celsius and methyl hydrazine (2 ml) was added. The solution was to stirred at 0 degrees Celsius for one hour and then at room temperature for 10 hours. The volatiles were removed by rotary evaporation. The viscous oily residue was dissolved in a small volume of methylene chloride and applied to a cartridge of silica gel. The cartridge was eluted using a gradient going from a 7:3 ratio of methylene chloride and acetone to a 2:8 ration of methylene chloride and acetone. The appropriate fractions were concentrated and triturated with methanol to produce a white solid (329 mg, 46%). $^1$H NMR (400 MHz, DMSO-d$_6$) δ ppm 1.77-1.86 (m, 2H) 2.4 (s, 2H) 3.48 (s, 1H) 3.61 (s, 1H) 3.69-3.76 (m, 5H) 6.37 (s, 1H) 7.04 (s, 1H) 7.10 (d, J=8.42 Hz, 1H) 7.14 (d, J=10.98 Hz, 1H) 7.26 (s, 1H) 7.40 (d, J=3.29 Hz, 1H) 7.42-7.50 (m, 4H) 7.53 (s, 1H). HRMS calc M+H, 412.1495, found 412.1555.

Example 3

Fluorescence Intensity 5-LO Enzyme Assay

Earlier compounds included in the references such as 4-(3-{[4-(1-methyl-1H-pyrazol-5-yl)phenyl]thio}phenyl)tetrahydro-2H-pyran-4-carboxamide ($IC_{50}$=867 nM in test conditions identical to those disclosed below) have been observed to inhibit recombinant human 5-LO enzyme at similar potency. The enzyme assay is based on the oxidation of the non-fluorescent compound 2',7'-dichlorodihydrofluorescein diacetate (H2DCFDA) to the fluorescent 2',7' dichlorofluorescein by 5-LO in an arachidonic acid-dependent reaction. Ester cleavage of the acetate groups of the substrate H2DCFDA must occur prior to oxidation. This is achieved through use of a crude cell lysate preparation of recombinant human 5-LO. The enzyme assay (40 L) contained 50 mM Tris (pH 7.5), 2 mM $CaCl_2$, 2 mM EDTA, 3 µM arachidonic acid (Nu-Chek Prep; #S-1133), 10 µM ATP, 10 µM H2DCFDA (Invitrogen; #D399), inhibitor (varying concentration) and recombinant human 5-LO enzyme (1.25 µL crude lysate per well).

Inhibitors (dissolved in DMSO) were plated into a 384-well assay plate (Corning #3654) at 1 µL followed by a 20 µL addition of a solution containing 5-LO enzyme and H2DCFDA. Enzyme and H2DCFDA were pre-incubated for 5 minutes to allow time for acetate group cleavage of the dye prior to addition to the assay plate. After a 10 minute preincubation of inhibitor and enzyme/dye mix, the assay was initiated by the addition of a substrate solution containing arachidonic acid and ATP. The enzymatic reaction was run for 20 min at room temperature and terminated by the addition of 40 µL of acetonitrile. Assay plates were read in a plate reader using standard wavelengths for fluorescein. $IC_{50}$s of inhibitors were calculated using a 4-parameter fit using 7 inhibitor concentrations in duplicate with 3-fold serial dilutions. Controls on each plate included no inhibitor (zero percent effect) and 25 µM 4-(3-(4-(2-methyl-1H-imidazol-1-yl)phenylthio)phenyl)-tetrahydro-2H-pyran-4-carboxamide (one hundred percent effect). The highest inhibitor concentration tested was typically 25 µM. The final DMSO concentration in the assay was 2.5%.

| COMPOUND | $IC_{50}$ |
|---|---|
| (Ia) | 204 nM |
| (Ib) | 229 nM |

Example 4

Emesis Evaluation

Earlier compounds had been observed to produce nausea and emesis in humans after oral administration at exposures similar to those expected for therapeutic inhibition of the 5-lipoxygenase enzyme for diseases such as asthma or inflammatory disorders. The occurrence of these gastrointestinal symptoms after administration of these compounds limited their clinical utility.

Experiments were undertaken to differentiate local gastrointestinal emetic stimuli during dissolution and absorption of an oral compound from emetic stimuli produced during systemic exposure through the bloodstream. Earlier, compounds were found to produce nausea and emesis through systemic exposure, rather than through local concentrations within the gastrointestinal tract at the sites of dissolution and absorption. This suggested that formulation modifications that alter the location of release or slow the dissolution of the compounds would not be effective in reducing gastrointestinal side effects. These findings were observed after 8-12 kg purpose-bred beagle dogs were administered 4-(3-{[4-(1-methyl-1H-pyrazol-5-yl)phenyl]thio}phenyl)tetrahydro-2H-pyran-4-carboxamide by IV infusion, using a loading dose followed by a slow infusion to attain a peak blood level over 30 minutes to 1 hour in duration. More specifically, compounds were diluted in phosphate buffered saline to a concentration where 10 ml/kg total volume was administered through an intravenous catheter using an infusion pump, with approximately 90% of the total dose being delivered in the first 5 minutes, and the remaining dose administered over the next 25 minutes. Similar delivery methods to produce an exposure that approximates the systemic pharmacokinetic profile seen with oral delivery are anticipated to give similar results. More rapid methods of administration and the resultant high plasma concentrations are not anticipated to discriminate useful compounds from non-useful compounds. For example, IV bolus administration may produce a higher peak plasma concentration and systemic gastrointestinal effects than those achieved for compounds that following absorption from the GI tract, would have acceptable peak plasma concentrations and therapeutic efficacy. During and after administration of the compounds, the dogs were observed for any undesirable clinical effects, most notably emesis or other signs of gastrointestinal distress. Periodic serum and plasma samples were obtained during the first 6 hours to document systemic inhibition of the 5-lipoxygenase enzyme as well as exposure levels of the compound. The presence of emesis with earlier compounds without any local dissolution or absorption in the gastrointestinal tract provided the opportunity to identify new compounds that did not have similar unwanted effects and would have increased utility in the therapy of inflammatory diseases such as asthma. In one study, 4-(3-(4-(2-methyl-1H-imidazol-1-yl)phenylthio)phenyl)-tetrahydro-2H-pyran-4-carboxamide was administered intravenously at 10 mg/kg, 30 mg/kg and 60 mg/kg as well as 30 mg per kg by the oral route. Emesis was observed in all dogs, with frequency of severity increasing with dose. In contrast, in another study, 4-(3-{[4-(1-methyl-1H-pyrazol-5-yl)phenyl]thio}phenyl)tetrahydro-2H-pyran-4-carboxamide was administered at a dose of 5 mg/kg IV resulting in an exposure that inhibited the 5-LO enzyme by 100% with no observed emesis. Further administration of 4-(3-{[4-(1-methyl-1H-pyrazol-5-yl)phenyl]thio}phenyl)tetrahydro-2H-pyran-4-carboxamide by the oral route at doses of 10 mg per kg and 100 mg per kg resulted in emesis in only one dog at 100 mg per kg. In another experiment, 4-(3-{[4-(1-methyl-1H-pyrazol-5-yl)phenyl]thio}phenyl)tetrahydro-2H-pyran-4-carboxamide was administered orally at doses of 100 mg per kg, 300 mg per kg, and 600 mg per kg, with emesis only observed in 2 dogs at 100 mg per kg and one dog at 300 mg per kg. No emesis was observed at 600 mg per kg.

These data from dogs suggest that efficacious levels of 4-(3-{[4-(1-methyl-1H-pyrazol-5-yl)phenyl]thio}phenyl) tetrahydro-2H-pyran-4-carboxamide can be reached in humans as measured by inhibition of 5-lipoxygenase, without a significant incidence of emesis.

This improved side effect profile represents an advance over 4-(3-(4-(2-methyl-1H-imidazol-1-yl)phenylthio)phenyl)-tetrahydro-2H-pyran-4-carboxamide, which caused nausea or emesis in 30% of human subjects in a clinical trial. It is predicted that the significant reduction of emesis in dogs by 4-(3-{[4-(1-methyl-1H-pyrazol-5-yl)phenyl]thio}phenyl)tetrahydro-2H-pyran-4-carboxamide will translate to reduction or elimination of nausea or emesis in humans.

Example 5

Eicosanoid Production from Human Whole Blood

Earlier compounds included in the references such as 4-(3-{[4-(1-methyl-1H-pyrazol-5-yl)phenyl]thio}phenyl)tetrahydro-2H-pyran-4-carboxamide ($IC_{50}$=261 nM in test conditions identical to those disclosed below) have been observed to inhibit the ionophore induced production of $LTB_4$ in human whole blood at similar potency. According to the established opinion in the field, this data indicates the ability of the compounds to inhibit the target (5-LO) in human whole blood. Human whole blood was collected from healthy or asthmatic human donors in 10 ml heparinized tubes (Vacutainer tubes; Becton Dickenson, Franklin Lakes, N.J.). Collected blood was pooled and 80 µl was dispensed into each well of 384 well polypropylene plates using a Multi-Drop™ 384-well dispenser (Titertek, Huntsville, Ala.). Varying concentrations of compounds were dissolved in DMSO then 2 µl/well was added to the blood using a PlateMate Plus™ automated pipetting station (Matrix Technologies, Hudson, N.H.). The compounds were preincubated with the blood at room temperature for 10 minutes followed by stimulation with 40 µl calcium ionophore (A23187, Sigma Chemical Co, St. Louis, Mo., Cat. # C-7522) and 30 µl arachidonic acid (S-1133, NU-Chek PREP, Inc., Elysian, MN, Cat. # S-1133) dissolved in 60% ethanol. After 15 min incubation at 37° C. in a shallow water bath, the blood was centrifuged at 800 g for 10 minutes at 4° C., the supernatants collected, and leukotriene and prostaglandin levels measured by ELISA according to the manufacturer's directions (Cayman Chemical Company, Ann Arbor, Mich.). The assay was performed at a final concentration of 2.5% DMSO. Results of this assay are shown as follows:

HWB/$LTB_4$: Ionophore Induced $LTB_4$ from Human Whole Blood

| Compound | $IC_{50}$ | $IC_{80}$ | $IC_{90}$ |
|---|---|---|---|
| (Ia) | 152 nM | 357 nM | 1310 nM |
| (Ib) | 135 nM | 397 nM | 716 nM |

Example 6

Carrageenan-Induced Eicosanoid Production in the Rat Air Pouch

Earlier compounds included in the references such as 4-(3-{[4-(1-methyl-1H-pyrazol-5-yl)phenyl]thio}phenyl)tetrahydro-2H-pyran-4-carboxamide (3 mpk=20% of control in test conditions identical to those disclosed below) have been observed to inhibit the production of carrageenan induced production of leukotrienes in the rat air pouch at similar potency. According to the established opinion in the field, this data indicates the ability of the compounds to inhibit the target (5-LO) in vivo. For a correct interpretation of the results, it is noted that the lower the % of control, the higher the activity of a test compound. Male Lewis rats (175-200 g), Charles River Laboratories, Wilmington, Mass.) were used in the study. Air pouches were produced by subcutaneous injection of 20 ml of sterile air into the intrascapular area of the back. Pouches were allowed to develop for 1 day. Animals (6 per group) were fasted with free access to water for 16 to 24 hours prior to drug administration. Drugs or vehicle were administered by gavage 1 hour prior to injection of 2 ml of a 1% suspension of carrageenan (FMC BioPolymer, Philadelphia, Pa., Cat. # GP209-NF) dissolved in saline into the pouch. At 3 hours post-carrageenan injection, 1 ml of 50 µg/ml calcium ionophore in saline (A23187, Sigma Chemical Co, St. Louis, M, Cat. #C-7522) was injected into the pouch and the pouch fluid collected 10 minutes later by lavage. The fluid was centrifuged at 3500 rpm for 10 minutes at 4° C., and the supernatants were collected for analysis. Leukotriene levels were quantitated by ELISA according to the manufacturer's directions (Cayman Chemical Company, Ann Arbor, Mich.).

| Dose mg/kg | (Ia) % of Control | (Ib) % of Control |
|---|---|---|
| Vehicle | 100 | 100 |
| 1 | 25.74 | 20.24 |
| 3 | 0 | 5.23 |
| 10 | 0 | 2.30 |

It is to be understood that the examples provided herein are illustrative only and not to be construed in a limiting sense.

The invention claimed is:

1. A compound of formula (I):

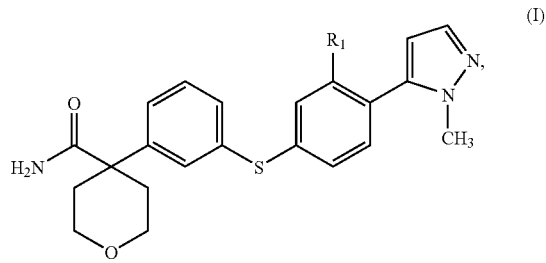

or a pharmaceutically acceptable salt or solvate thereof, wherein $R_1$ is F or H.

2. The compound of claim 1 of formula (Ia):

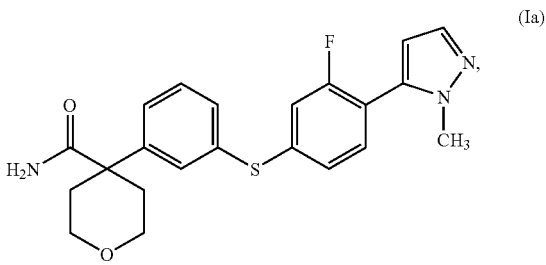

or a pharmaceutically acceptable salt or solvate thereof.

3. The compound according to claim 1 of formula (Ib):

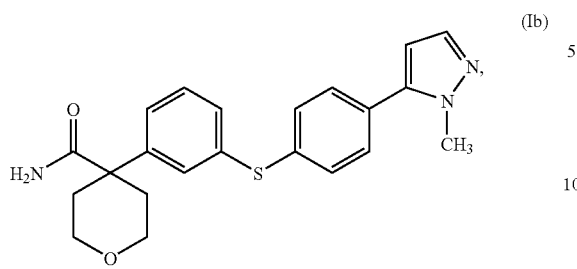
(Ib)

or a pharmaceutically acceptable salt or solvate thereof.

4. A method of treating asthma, allergic rhinitis or chronic obstructive pulmonary disease (COPD) in a mammal having asthma, allergic rhinitis or chronic obstructive pulmonary disease, the method comprising administering to the mammal a compound of claim 1 or a pharmaceutically acceptable salt or solvate thereof.

5. The method of claim 4, wherein said asthma
atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome or bronchiolytis.

6. A pharmaceutical composition comprising a compound of claim 1 or a pharmaceutically acceptable salt or solvate thereof and a pharmaceutically acceptable excipient.

7. A process for preparing a compound of claim 2, said process comprising the steps of contacting a compound of formula (V):

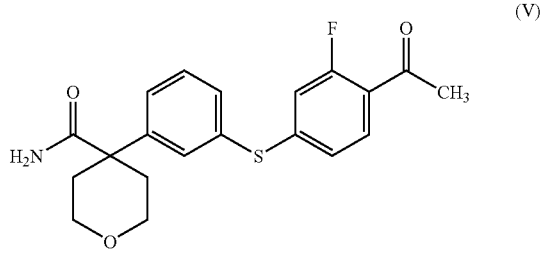
(V)

with N,N'-dimethylformamide dimethyl acetal followed by treatment with methylhydrazine.

8. A process for preparing a compound of claim 3, said process comprising the step of contacting a compound of formula (II):

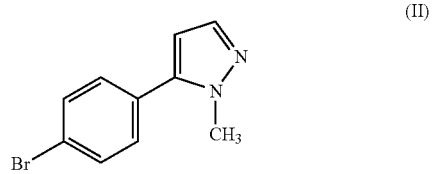
(II)

with a compound of formula (VII)

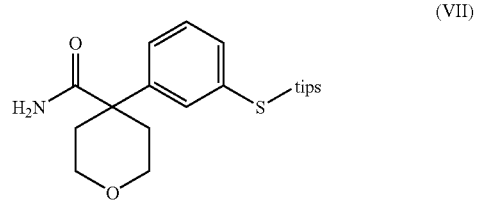
(VII)

in the presence of a suitable catalyst.

9. The compound of formula (V):

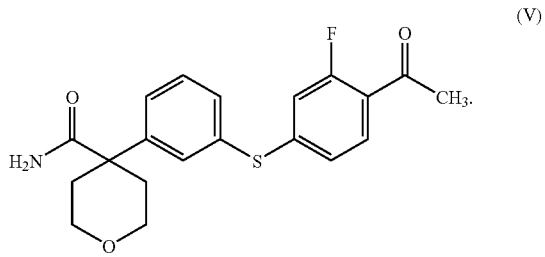
(V)

10. The pharmaceutical composition of claim 6 further comprising a histamine antagonist.

11. The pharmaceutical composition of claim 10 wherein said histamine antagonist is a histamine ($H_1$) antagonist.

12. A method of treating asthma, allergic rhinitis or chronic obstructive pulmonary disease (COPD) in a mammal having asthma, allergic rhinitis or chronic obstructive pulmonary disease, the method comprising administering to the mammal a pharmaceutical composition of claim 10.

13. The method of claim 12, wherein said asthma is atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non- allergic asthma, incipient asthma, wheezy infant syndrome or bronchiolytis.

* * * * *